US007164000B2

(12) United States Patent
Lusso et al.

(10) Patent No.: US 7,164,000 B2
(45) Date of Patent: Jan. 16, 2007

(54) RANTES MUTANTS AND THERAPEUTIC APPLICATIONS THEREOF

(75) Inventors: Paolo Lusso, Milan (IT); Simona Polo, Milan (IT)

(73) Assignee: Fondazione Centro San Raffaele Del Monte Tabor, Milan (IT)

( * ) Notice: Subject to any disclaimer, the term of this patent is extended or adjusted under 35 U.S.C. 154(b) by 437 days.

(21) Appl. No.: 10/400,487

(22) Filed: Mar. 28, 2003

(65) Prior Publication Data

US 2003/0216549 A1 Nov. 20, 2003

Related U.S. Application Data

(62) Division of application No. 09/581,070, filed as application No. PCT/EP98/08354 on Dec. 21, 1998, now Pat. No. 6,608,177.

(30) Foreign Application Priority Data

Dec. 23, 1997 (IT) .............................. MI97A2865
Aug. 7, 1998 (IT) .............................. MI98A1866

(51) Int. Cl.

*A61K 38/19* (2006.01)
*A61K 38/16* (2006.01)
*A61K 45/00* (2006.01)
*C12N 15/00* (2006.01)
*C12N 15/11* (2006.01)
*C12N 15/12* (2006.01)
*C12N 15/19* (2006.01)
*A01N 63/00* (2006.01)

(52) U.S. Cl. .................... 530/300; 424/85.1; 424/85.2; 424/93.1; 435/320.1; 435/69.1; 536/23.1

(58) Field of Classification Search ................ 530/350, 530/351, 300; 424/85.1, 85.2; 435/320.1, 435/69.1

See application file for complete search history.

(56) References Cited

U.S. PATENT DOCUMENTS 6,159,711 A 12/2000 Proudfoot et al.

FOREIGN PATENT DOCUMENTS

WO WO 96/17935 A 6/1996
WO WO 97/44462 A 11/1997
WO WO 98/13495 A1 4/1998

OTHER PUBLICATIONS

Lazar et al. Molecular and Cellular Biology 1988, vol. 8, No. 3, pp. 1247-1252.*
Smilek et al. Proc. Natl. Acad. Sci. USA, 1991, vol. 88, pp. 9633-9637.*
Proudfoot et al. J. Biochem. Chemis. 1999, vol. 274, No. 45, pp. 32478-32485.*
Littman D. Cell 1998, vol. 93, pp. 677-680.*
Skelton et al. Biochemistry 1995, vol. 34, pp. 5329-5342.*
Schall et al. J. Immunol. 11988, vol. 141, No. 3, pp. 1018-1025.*
Oravecz et al., *J. Exp. Med.*, 186:1865-1872 (1997).
Mosier et al., *J. Virol.*, 73:3544-3550 (1999).
Trkola et al., *J. Virol.*, 73:6370-6379 (1999).
Shepard et al., *Nature*, 294:563-565 (1981).
Deepika R. Pakianathan et al., Distinct but overlapping epitopes for the interaction of a CC-chemokinewith CCR1, CCR3, and CCR5, *Biochemistry*, 36:99642-9648 (1997) Easton, PA, US.
Chun-Wa Chung et al, The three-dimensional solution structure of rantes, *Biochemistry*, 34:9307-9314 (1995) Easton, PA, US.
Gong JH et al., Rantes and MCP-3 antagonists bind multiple chemokine receptors, *Journal of Biological Chemistry*, 271(18)10521-10527 (1996).
Skelton NJ et al., Proton NMR assignments and solution conformation of rantes, a chemokine of the C—C type, *Biochemistry*, 34(16)5329-5342 (1995).

* cited by examiner

*Primary Examiner*—Bao Qun Li
(74) *Attorney, Agent, or Firm*—Browdy & Neimark, PLLC

(57) ABSTRACT

RANTES mutants characterised by the substitution or addition of amino acids at the N-terminal of RANTES wild-type sequence and in the N-loop and/or 40's loop regions of RANTES wild-type sequence, and their use as anti-HIV, anti-allergic or anti-inflammatory agents.

7 Claims, 6 Drawing Sheets

RANTES MUTANTS AND THERAPEUTIC APPLICATIONS THEREOF

The present invention provides RANTES mutants with reduced pro-inflammatory activity, increased HIV-suppressive activity, and antagonistic activity to wild-type chemokines.

Chemokines are small proteins involved in inflammatory mechanisms and in physiologic circulation of hemopoietic cells. Several studies have shown the important role of chemokines in recruiting leucocytes in inflammatory and autoimmune diseases, like rheumatoid arthritis, or during allergic reactions, like in asthma (Schall, T. J. The chemokines. In: The cytokine handbook, A Thompson ed. Academic Press, New York, 1994, p. 419–460). Furthermore, some chemokines have been recently identified as potent natural inhibitors of human immunodeficiency virus (HIV) infection (Science 270, 1811–1815, 1995). Chemokines activity is due to their interaction with receptors having different specificity and expressed on the cell surface. Some of these receptors function as co-receptors for HIV-virus (Science 272, 872–877, 1996; Science 272, 1955–1958, 1996). The differential use of such co-receptors, particularly CCR5 the specific receptor for RANTES, MIP-1α and MIP-1β, and CXCR4, the SDF-1 specific receptor, represents a major determinant of the biological diversity among HIV strains. HIV-1 strains unable to infect continuous CD4+ T-cell lines, commonly involved in viral transmission and predominating during the asymptomatic phase of the infection, use primarily CCR5 as a co-receptor and are invariably sensitive to inhibition by CCR5-binding chemokines (Nature Med., 3:1259–1265, 1997). The most effective such chemokine, RANTES, is therefore under investigation for the development of novel anti-HIV therapies (Nature, 383: 400, 1996). RANTES is a chemokine which belongs to the C—C family and is 68 amino acids long. Its sequence has been reported in J. Immunol. (1988).

WO 96/17935 discloses RANTES molecules which are modified at the N-terminus through the addition of an amino acid such as methionine, leucine or glutamine, as antagonists of RANTES or MIP-1α. In particular, the use thereof for the treatment of asthma, allergic rhinitis, atopic dermatitis, atheroma-atherosclerosis or rheumatoid arthritis is described.

Further, Elsner J. et al. in "European Journal of Immunology, Vol. 27, 2892–2898 (1997)", and WO 96/17934, disclose the antagonistic activity of the Met-RANTES peptide.

The use of wild-type RANTES and of other chemokines of the same family in the treatment of allergic diseases, has been also described in WO 94/07521 and WO 94/21277.

WO 97/25350 discloses disaggregated mutants of MIP-1α or LD78 having HIV suppressive activity, whereas WO 98/13495 discloses human RANTES mutants unable to aggregate under physiologic ionic strength and which exhibit antiviral activity. Surprisingly now, it has been found that the addition of at least one amino acid at the N-terminus, and/or the substitution of one or more amino acids in the N-terminal region comprised between amino acids 1 and 11 of the mature form of the human chemokine RANTES, and/or in the "40's-loop" region, extending from Thr 43 to Asn 46, provides a notably higher efficacy towards different HIV isolates, both in primary mononucleated blood cells and in macrophages, a reduced pro-inflammatory activity and a potent antagonistic activity, as compared to the wild-type molecule. In particular, the mutants of the invention competitively antagonise wild-type RANTES, MIP-1α or MIP-1β, and, with a comparable mechanism, the interaction between the HIV virus and a chemokine receptor. Preferably, one or more of the amino acids: Ser 1, Ser 4, Ser 5, Tyr 3, Asp 6, Tyr 14, Arg 17, Arg 44, Lys 33, Lys 45 and Asn 46 are mutated, with respect to the wild-type human form described in J. Immunol. 141:10181025, 1988, as reference molecule. Preferably, the amino acids Ser 1, Ser 4, Ser 5, Tyr 3 are replaced by neutral or hydrophobic amino acids, Asp 6 is replaced by a positively charged amino acid, Tyr 14 by a hydrophobic aromatic, Arg 17, Lys 33, Arg 44, Lys 45 and Asn 46 by a small sized hydrophobic amino acid.

The following mutations are more preferred: Ser 1 with Cys, Ser 4 with Cys, Ser 5 with Cys, Tyr 3 with Ala, Asp 6 with Arg, Tyr 14 with Phe, Arg 17, Lys 33, Arg 44, Lys 45 and Asn 46 with Ala. A first group of mutants according to the invention is characterised by a triple mutation selected from a) Ser 1 with Cys; Ser 5 with Cys; Asp 6 with Arg, or b) Ser 1 with Cys; Ser 5 with Cys; Arg 17 with Ala, or c) Ser 1 with Cys; Ser 5 with Cys; Arg 44 or Lys 45 or Asn 46, with Ala. A second group is characterised by a double mutation selected from a) Ser 1 and Ser 5 with Cys, or b) Ser 1 and Ser 4 with Cys, or c) Ser 1 with Cys and Arg 44 with Ala, or d) Asp 6 with Arg and Arg 44 with Ala. A third group is characterised by a single mutation selected from a) Ser 1 with Cys, b) Tyr 3 with Ala, c) Asp 6 with Arg, d) Tyr 14 with Phe, e) Arg 17 with Ala, f) Lys 33 with Ala, g) Arg 44 with Ala, h) Lys 45 with Ala, i) Asn 46 with Ala. Furthermore, the above mutants can be added with up to two amino acids at the N-terminus, which are preferably selected from Leu, Ala, Cys or Trp. For example, Ser 4 may be replaced by Cys and simultaneously an additional Cys may be added at the N-terminus. In particular, the single mutant Cys 1 or −1, which contains a free —SH group, may represent an optimal substrate for further chemical modifications.

According to other aspects, the invention provides wild-type RANTES, having no internal amino acid mutations but bearing an additional amino acid at the N-terminus, which is preferably Cys, said RANTES derivatives being endowed with anti-HIV and anti-inflammatory activity, and the use of wild-type RANTES added with a Leu at the N-terminus (Leu(0) RANTES) as anti-HIV agent.

It is possible that the properties of some mutants according to the invention, in particular those carrying 1 or 2 additional Cys, are determined by structural modifications due to the formation of a new disulphide bond. Considering the structure of RANTES (Biochem. 1995, 34:9307–9314) or the structure of homologous molecules like SDF-1 (EMBO J., 16:6996:7007, 1997), it is also possible that the N-terminal or N-loop regions contribute to form the three-dimensional site of interaction with the specific membrane receptor.

According to another aspect, the invention provides for peptides corresponding to RANTES fragments in the N-terminal, N-loop and/or "40's-loop" regions, said peptides contain the described mutations and competitively antagonise wild-type RANTES, MIP-1α or MIP-1β, or the interaction between HIV virus and a chemokine receptor.

According to other aspects, the invention provides nucleotide sequences encoding for the described mutants, the expression vectors comprising such nucleotide sequences, chimeric or fusion proteins which comprise a sequence corresponding to the invention mutants and a carrier sequence, for example a sequence aimed at improving the pharmacokinetic properties of active peptides or proteins; furthermore, the invention provides the use of such RANTES mutants as anti-HIV agents as well as anti-inflammatory, anti-allergic or anti-asthmatic agents.

By the term RANTES, any polypeptide functionally equivalent to the human RANTES is meant, as well as equivalent proteins derived from cross-reactive species, as well as variants and allelic forms thereof which may differ from the standard sequence reported in J. Immunol. 141: 1018–1025, 1988.

The mutants of the invention may be prepared by conventional techniques of DNA cloning, recombination and in vitro expression, using suitable synthetic oligonucleotides, for example with techniques of site-directed mutagenesis or by the DNA Polymerase Chain Reaction (PCR). The resulting DNA is then inserted into an appropriate expression vector for a prokaryotic or an eukaryotic host. Alternatively, mutants can be prepared according to conventional methods of peptide synthesis.

For the envisaged therapeutical purposes, the mutants of the invention will be administered in form of suitable pharmaceutical compositions by the parenteral, sublingual, intranasal, inhalatory or topical route of administration, prepared according to conventional techniques, which are suitable for polypeptide or protein active substances.

The amount of polypeptide to administer will be sufficient to cause a significant inhibition of HIV infection or replication, or reduction of inflammatory responses, such as in rheumatoid arthritis, or in degenerative diseases such as atherosclerosis, or in allergic diseases such as asthma, rhinitis and dermatitis. The specific dosage will be determined on the basis of clinical trials and will depend on a number of factors, such as conditions, sex, age and weight of the patient and severity of the condition. The mutants of the invention will be also used in the prevention of HIV infection in individuals potentially exposed to the infection.

Furthermore, the DNA encoding such mutants, which are produced as recombinant proteins in eukaryotic hosts and do not require further chemical modification, may be inserted into gene-therapy vectors (derived for instance, from mouse or human retroviruses, like MuLV or HIV, or Herpes-virus, like HHV-7, or Adenovirus) which allow their production directly into the tissue where the treatment is needed (i.e. lymphonodes, joints, etc.).

Figure 1:
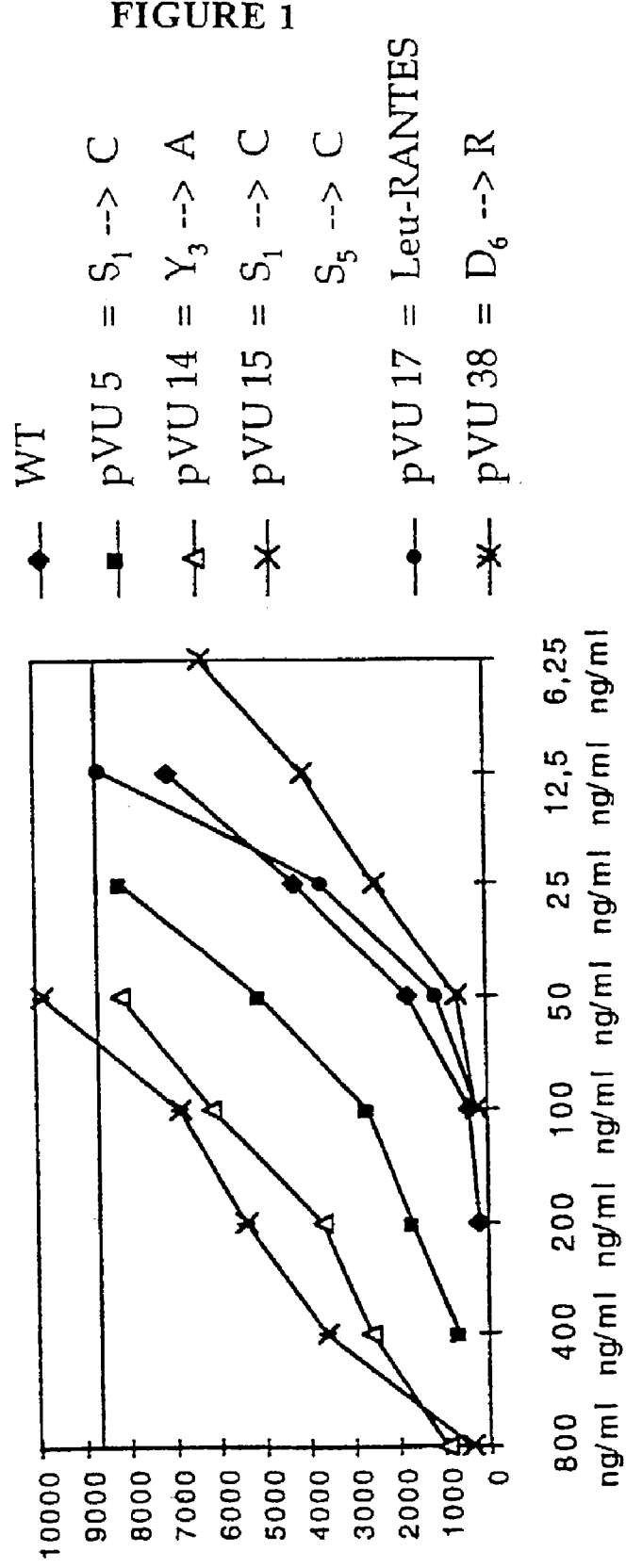
FIG. 1 is a graph of the ability of wild-type and mutant RANTES to inhibit infection of peripheral mononuclear cells (PBMC) by the HIV-1 BaL viral strain.
Figure 2:
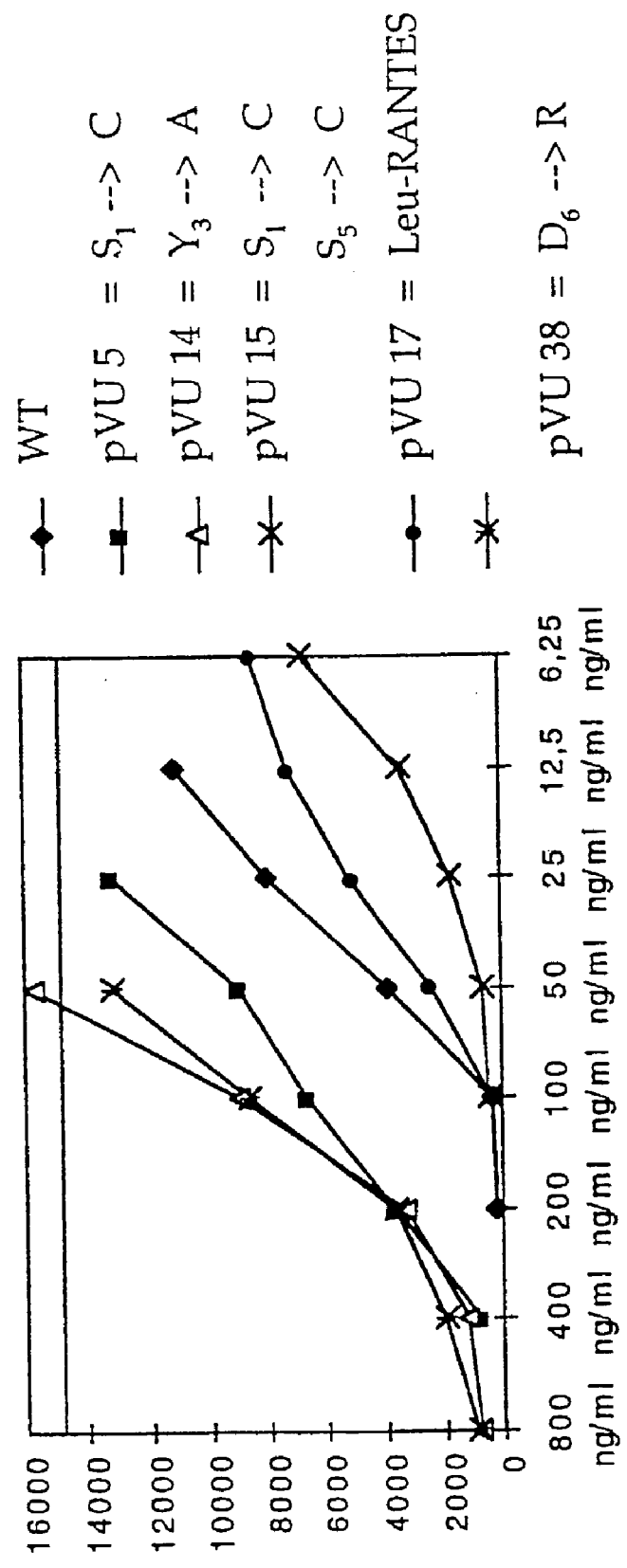
FIG. 2 is a graph of the ability of wild-type and mutant RANTES to inhibit infection of PBMC by the HIV-1 6366 viral strain.
Figure 3:
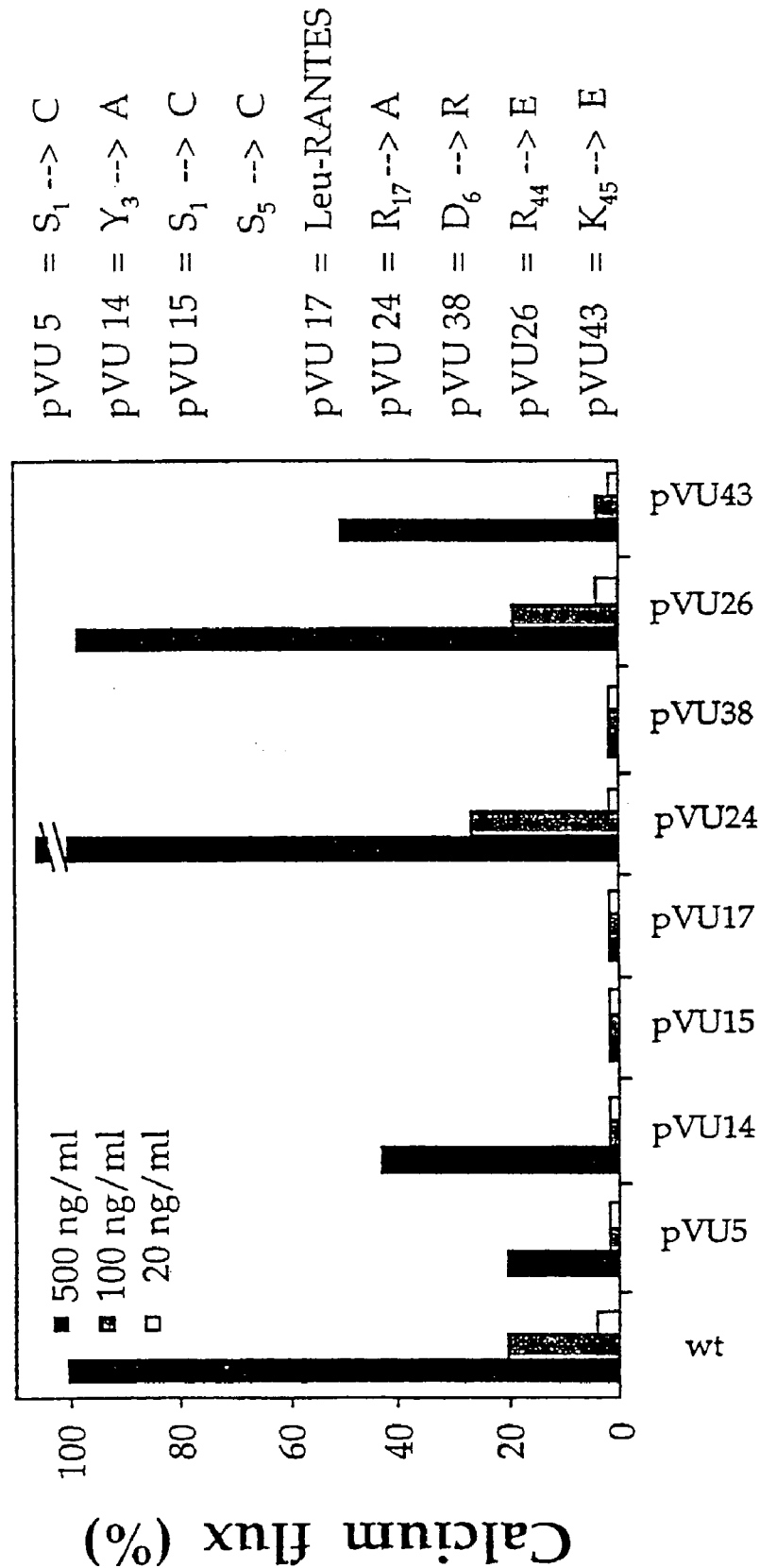
FIG. 3 is a graph showing calcium mobilization/flux induced by wild-type and mutant RANTES.
Figure 4:
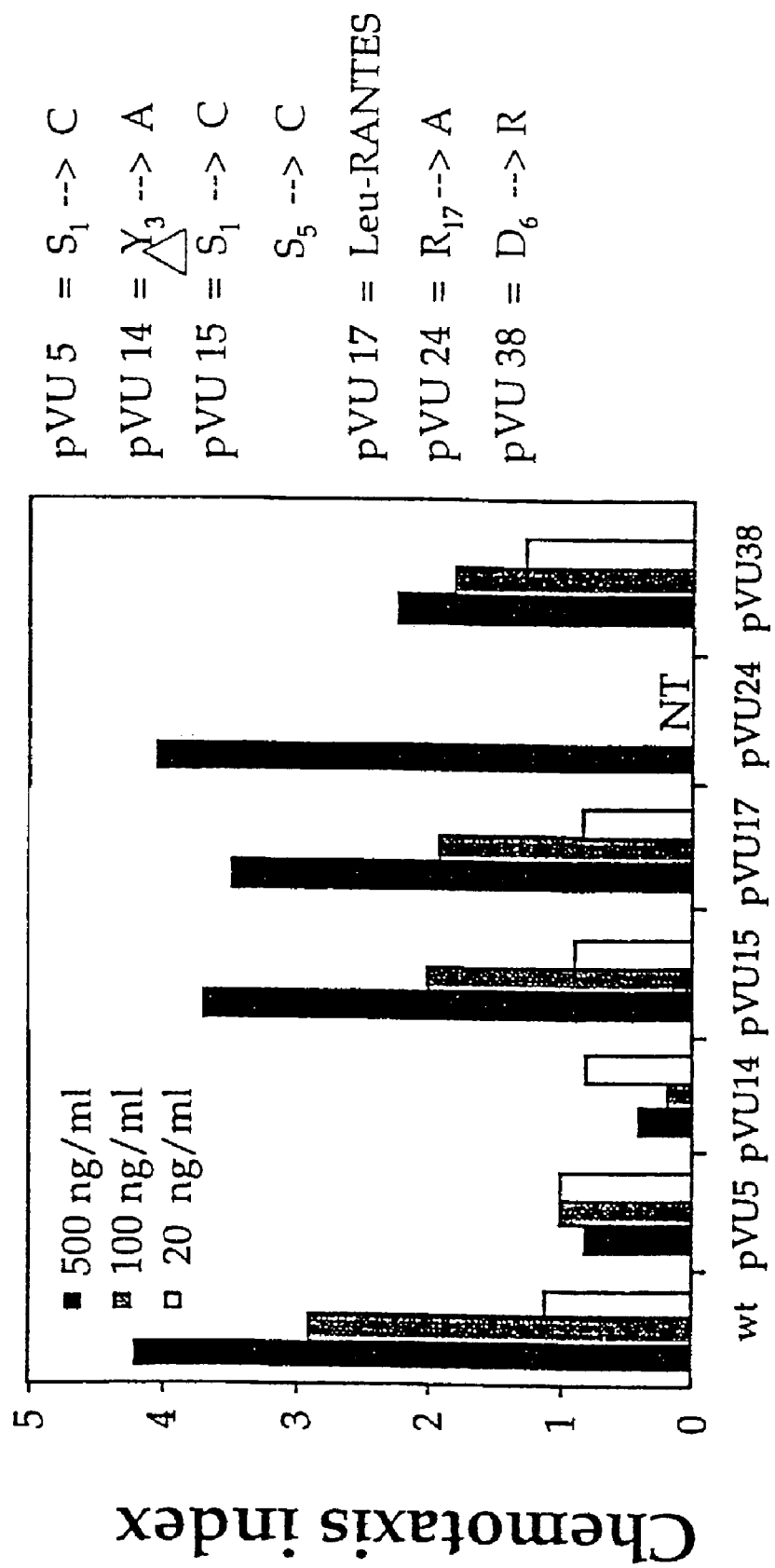
FIG. 4 is a graph showing monocyte migration in the presence of mutant RANTES, as measured by the chemotactic index.
Figure 5:
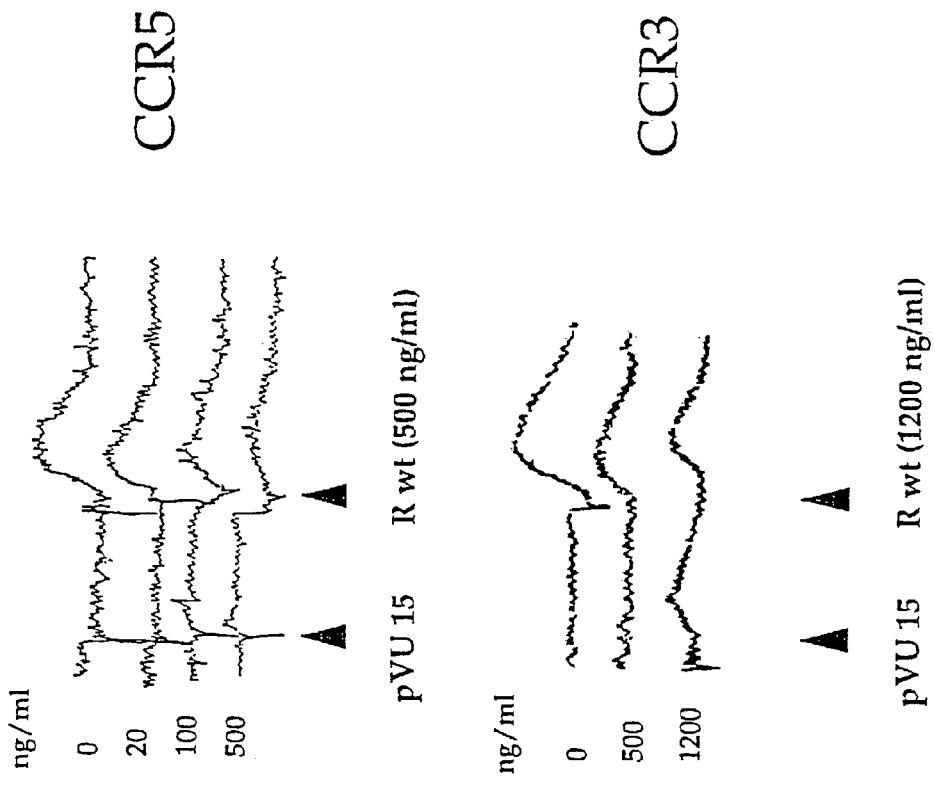
FIG. 5 is a graph showing CCR3 and CCR5 receptor desensitization in the presence of mutant RANTES pVU15.
Figure 6:
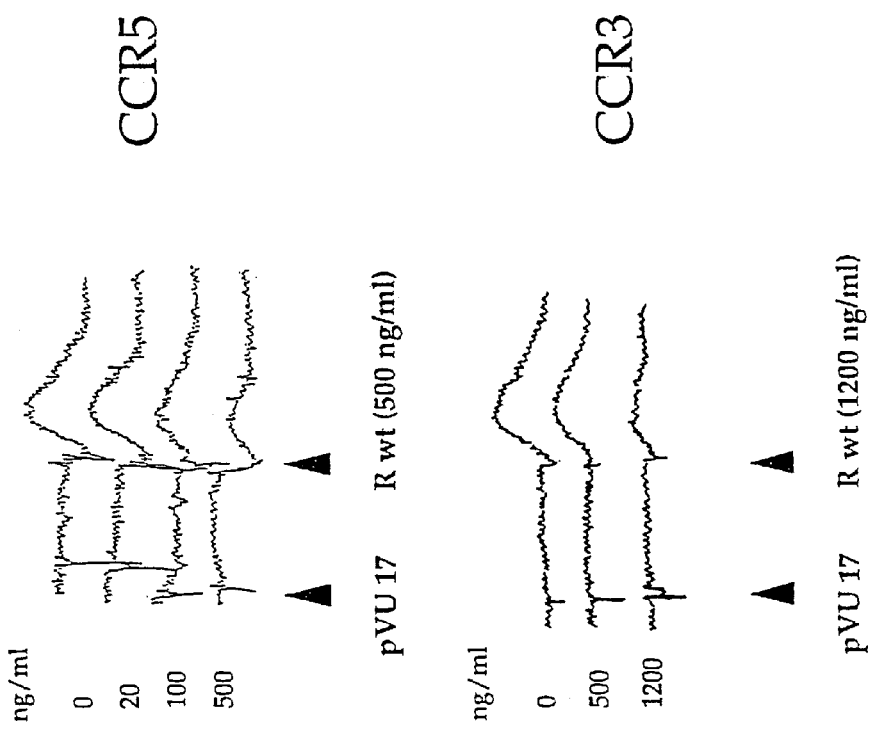
FIG. 6 is a graph showing CCR3 and CCR5 receptor desensitization in the presence of mutant RANTES pVU17.

The following examples illustrate the invention in more detail.

EXAMPLE 1

Cloning and Mutagenesis of the RANTES Sequence

Total RNA was extracted according to conventional techniques (Maniatis) from CD8+ T human lymphocytes purified by absorption with the anti CD8 antibody (Sigma C7423) bound to magnetic beads. The cDNA resulting from reverse transcription, using an oligo-dT as primer, was used for a PCR reaction (Polymerase Chain Reaction) with 2 oligonucleotide primers capable of amplifying the whole region coding for RANTES (434 bp):

(SEQ ID NO:1)
P1=5'-AC<u>GAATTC</u>ACAGGTACCATGAAGGTCTCCGCG;

(SEQ ID NO:2)
P2=5'-GT<u>GGATCC</u>TTTTTGTAACTGCTGCTCGTCGTGGT

Primers were designed so as to contain the restriction sites underlined in the P1 and P2 sequences, EcoRI (P1) at 5' and BamHI (P2) at 3', respectively. After amplification, the PCR product was digested with the EcoRI and BamHI restriction enzymes, purified from the gel by a QIAEX (Promega) column and re-ligated to the pUC18 vector DNA (Promega), digested in the polylinker with the same enzymes.

The eligated DNA was then used to transform *E. coli* competent cells (JM109). After selection of some ampicillin resistant clones, the DNA was sequenced to confirm the identity of the insert. Plasmid DNA was used for PCR mutagenesis, according to the procedure called "overlap extension" (Gene, 1991, 67:70). Such a technique allowed the production of single and multiple mutations in the same gene, by the use of common primers (which anneal to the sequence of the vector: A, B, C) and a series of primers specific for the various mutations. The sequences of the common primers are as follows:

(SEQ ID NO:3)
primer A: 5'-CAATATGTTGCCGGCATAGTACGCAGC (SEQ ID NO:4)
primer B: 5'-GGATCAGATTTGCAGCGGCCG (SEQ ID NO:5)
primer C: 5'-GTGGATCCTTTTTGTAACTGCTGCTCGTCGTGGT For the construction of pVU5 plasmid, the specific oligo Cys1 was used (5'-GGGTGTGGTGTCCGAGGAATATGGG<u>C</u>AGGCAG); SEQ ID NO:6). Such primer contains a single base mutation (C instead of G), which determines the substitution of Ser with Cys in position 1.

The specific oligo Tyr3 was used for the construction of pVU14 plasmid (5'-GTCCGAGGAA<u>GC</u>TGGGGAGGCAGATG; SEQ ID NO:7). Such primer introduces a two bases substitution (GC instead of TA), which determines the substitution of Tyr with Ala in position 3.

The oligo Cys1–Cys5 was used for the construction of pVU15 plasmid (5'-GGGTGTGGTGTC<u>GC</u>AGGAATATGGG<u>C</u>AGGCAG; SEQ ID NO:8), which incorporates a two base substitution (GC instead of CG), in addition to the substitution of primer cys1 (C instead of G). This determines the double substitution of Ser with Cys in positions 1 and 5.

The specific oligo Arg17
(5' CACGGGGCAGTGGG<u>GC</u>GGCAATGTAG-GCAAAGC; SEQ ID NO:9) was used for the construction of pVU24 plasmid. Such primer produces two base substitutions (GC instead of CG) which determine the substitution of Arg with Ala in position 17.

The specific oligo Asp6
(5'-CAGGGTGTGTGGTGC<u>C</u>GCGAGGAATATGGGGA; SEQ ID NO:10) was used for the construction of pVU38 plasmid. Such primer produces two base substitutions (CG instead of TG) which determine the substitution of Asp with Arg in position 6.

The specific oligo Arg44 (5'-GGCGGTT<u>C</u>TTTTCGGTGACAAAGACGAC; SEQ ID NO:11) was used for the construction of pVU26 plasmid. Such primer produces a two base substitutions (TC instead of CG) determining the substitution of Arg 44 with Glu. A second mutant for this position (Arg44-Ala) was produced with a new oligo having the same sequence except for the double underlined T, substituted in G.

The specific oligo Lys45 (5'-CTTGGCGGTT<u>C</u><u>T</u>CTCGGGTGACAAAGACG; SEQ ID NO:12) was used for the construction of pVU43 plasmid. Such primer produces a single base substitution (C instead of T, underlined) which determines the substitution of Lys with Glu in position 45. A second mutant for this position (Lys 45-Ala) was produced with a new oligo having the same sequence except for the double underlined T, substituted in G.

The specific oligo Leu-R was used for pVU17 mutant preparation (5'-ATATGGGGATAAGGCAGATGCAG-GAGCGCA; SEQ ID NO:13). In this primer a three nucleotides insertion at the 5' of the molecule is added, before the first naturally occurring codon. The antisense triplet encodes for the additional N-terminal Leucine.

The specific oligo Tyr14 (5'-TGGGCGGGCAATGGCGGCAAAGCAGCAGGG; SEQ ID NO: 14) was used for the construction of pVU22 plasmid. Such primer introduce the substitution of Tyr14 with Phe in position 14. A second mutant for this position (Tyr 14-Ala) was also produced.

Other mutants were prepared using the following oligo:
Oligo Cys1–Cys4:
5'-GGGTGTGGTGTCCGAG<u>C</u>AATATGGG<u>C</u>AGGCAG (SEQ ID NO: 15); the substitution of two G with two C (underlined) produces the substitution of two Ser (in positions 1 and 4) with two Cys;
Oligo Cys0–Cys4:
CCGAG<u>C</u>AATATGGGGA<u>GC</u>AGGCAGATGCAGGAG (SEQ ID NO: 16); the substitution of G with C (underlined) produces the substitution of Ser (in position 4) with Cys, whereas the insertion of GCA produces the insertion of an additional Cys in position 0;
Oligo Leu-Ala:
5'-ATATGGGGA<u>GGCTAA</u>GGCAGATGCAGGA (SEQ ID NO: 17); the insertion of 6 nucleotides (GGCTAA) upstream the codon of Ser 1 produces the insertion of Leu and Ala in positions −1 and 0, respectively.
Oligo Tyr 14:
5'-TGGGCGGGCAATG<u>T</u>AGGCAAAGCAGCAGGG (SEQ ID NO: 18); the substitution of A in T (underlined) allows the substitution of Tyr14 in Phe.

The PCR products were purified and cloned into the BGlII-BamHI site of the pUC18 vector. The recombinants were sequenced to confirm their identity and check for undesired mutations introduced during the cloning procedures.

EXAMPLE 2

Expression and Purification of the Recombinant Molecules in Baculovirus

The Baculovirus expression system has been known for some years. It is based on the expression machinery of the Autographa californica Nuclear Polyhedrosis Virus (AcNPV). In this system the gene of interest are placed, by homologous recombination, under the control of the polyhedrin gene promoter, which is a non-essential gene but expressed at very high levels during the late phase of viral infection.

The choice of such a system involves a number of advantages, the main ones being: 1) high expression levels; 2) functionality of the recombinant protein, which is correctly processed and folded (most modifications correspond to the ones introduced by mammalian cells); 3) extracellular secretion due to the signal peptide (O'Reilly D R, Miller L K, Luckow V A, "Baculovirus expression vectors—A laboratory. manual", Oxford University Press, 1994).

In order to express RANTES and its mutants in this system, the corresponding DNA were cut out from pUC18 and cloned into the BamHI-EcoRI site of pVL1392 plasmid polylinker region (Pharmingen), under the control of the polyhedrin promoter. This plasmid also contains downstream of the cloned insert, an AcNPV homology region for homology recombination. An Autographa californica continuous cell line (SF9, Pharmingen) was transfected, using the calcium-phosphate co-precipitation, with the DNA of the recombinant plasmids and with the Baculovirus DNA containing a lethal deletion (BaculoGold™ DNA, Pharmingen). Only a homologous recombination leading to the substitution of the polyhedrin gene with the DNA of the interesting mutants provides vital viral particles (Gruenwald S, Heitz J, "Baculovirus expression vectors: procedures and methods manual", Pharmingen, 1993). The supernatant of the transfected cultures was then collected at the 3rd day, diluted and used to infect new SF9 cultures, thereby obtaining the viral lineage from a single infectious particles (end-point dilution). As expected, the RANTES protein and its mutants are secreted and their expression levels may be evaluated by a commercial ELISA test (R&D). The viral DNA was extracted from the potential recombinants, as detected by ELISA, and sequenced by PCR (Cycle Sequencing, Amersham) to confirm that the mutations had also occurred in the viral lineage. The selected viral stock was subsequently subjected to repeated cycles of infection and amplification in SF9 cells, to obtain high titer supernatants. These supernatants were used for the production of recombinant chemokines on a large scale, infecting a continuous Trichoplusia cell line (High Five, Invitrogen). These cells are capable of growth in a serum-free medium, simplifying the following protein purification procedures. $1.5 \times 10^8$ cells were infected with $1.5 \times 10^9$ vital viral particles in a final volume of 200 ml. At the $4^{th}$ infection day the supernatant was collected, filtered (0.45 u) and the mutants purified on heparin columns. After repeated washing with PBS, the column was eluted with PBS+1.5 M NaCl in 10 ml. An aliquot of the eluate was subjected to electrophoresis on acrylamide gel SDS-PAGE and stained with Coomassie blue, thus evaluating a 90% purity of the recombinant proteins. The eluate was subsequently dia-filtered to remove the present salts and concentrated (Centricon, cut-off 3000, Millipore). The final quantification of RANTES and its mutants was performed by an ELISA kit for the quantitative determination of RANTES (R&D) and confirmed by Western blot and capillary electrophoresis.

EXAMPLE 3

Inhibition of Viral Infection

The ability of the mutants obtained as in Example 2, to inhibit infection by the prototypic macrophage-tropic viral strain, HIV-1BaL, was measured in primary cultures of activated peripheral blood mononuclear cells (PMBC). The procedure used to infect PBL and to evaluate p24 antigen production has been already described in the literature (Scarlatti et al., Nature Medicine, 1997). The dose inhibiting viral proliferation by 90% (ID90) was remarkably lower for pVU15 as compared to wild-type RANTES which has an ID90 of 96 ng/ml (FIG. 1). The suppressive activity of pVU5, pVU14, pVU15, pVU24 and pVU38, was confirmed in another HIV strain, isolated from a patient with asymptomatic infection (HIV-1 6366) and passaged only once in peripheral blood mononuclear cells (FIG. 2): as for the BaL strain, this isolate depended upon CCR5 co-receptor usage (ibid.). The antiviral activity of the polypeptides of the invention, expressed as relative potency with respect to wild-type RANTES (ID90 RANTES/ID90 mutant) is illustrated in the following table.

TABLE

Relative antiviral activity of RANTES mutants (fold increase compared to wild-type RANTES)

| | | PBMC | | MDM |
|---|---|---|---|---|
| Derivatives | Mutations | HIV-1BaL | HIV-1 6366 | HIV-1BaL |
| PVU 5 | S1 → C | 0.24 | 0.23 | 0.25 |
| PVU 14 | Y3 → A | 0.22 | 0.10 | 0.23 |
| PVU 15 | S1 → C<br>S5 → C | 3.07 | 3.3 | 4.5 |
| PVU 24 | R17 → A | 1.09 | 1.30 | Nt |
| PVU 38 | D6 → R | 0.14 | 0.13 | Nt |
| PVU 26* | R44 → E | 3.16 | Nt | Nt |
| PVU 43* | K45 → E | 1.44 | Nt | Nt |
| PVU 22 | Y14 → F | 10.0 | 2.5 | Nt |
| PVU 17 | L added | 4.6 | 1.9 | 11.0 |

*The antiviral activity of pVU26 and pVU43 mutants is expressed as relative potency with respect to wild-type RANTES (RANTES ID50/mutant ID 50).

EXAMPLE 4

Pro-Inflammatory Activity

The ability of the RANTES mutants to mobilise intracellular calcium, which is induced by G-protein-coupled receptor activation and it is connected to the efficacy of signal trasduction of various ligands, was studied.

Cells were loaded with Fura-2 for one hour and stimulated by mutants at different concentrations. The effect was measured using a fluorimeter and calculated as the % increase of intra-cellular calcium. Wild-type RANTES induced a dose-dependent calcium mobilisation in U87-CD4 cells expressing CCR5 but not in CCR5-negative cells used as the control. Among pVU5, pVU14, pVU15, pVU24, pVU38, pVU26 and pVU43 tested mutants, only pVU38 pVU15 and pVU17 did not induce calcium mobilisation. pVU5, pVU14 and pVU43 had an efficacy lower than wild-type RANTES, as shown in FIG. 3.

The ability of the polypeptides of the invention to induce chemotaxis of primary human lymphocytes and monocytes was also measured, which ability can be mediated by different RANTES receptors, especially by CCR1.

Monocyte migration was assayed using a modification of the Boyden chamber (48 well Transwell(™), Costar). After 2 hours incubation in the presence of mutants at various concentrations, the filter was removed and migrated cells counted with a FACS. The chemotactic index represents the ratio of the number of cells that migrated in the presence of mutants to that due to the spontaneous migration. All the mutants except pVU5 and pVU14, induced monocyte chemotaxis, but at high concentrations, ranging from 100 to 500 ng/ml, pVU38 mutant exhibited an efficacy clearly lower than wild-type RANTES (FIG. 4).

Thus, whereas the ratio of the minimal chemotactic dose to the 90% HIV-suppressive dose in PBMC was between 8 and 50 for the mutant, it was between 1.0 and 2.9 for wild-type RANTES.

EXAMPLE 5

RANTES Antagonistic Effect

The ability of the mutant pVU15 and pVU17 to antagonise CCR3- and CCR5- receptor activation by wild-type RANTES, was studied in terms of intracellular calcium mobilisation.

When added immediately prior to the wild-type molecule, pVU15 reduced the response to wild-type RANTES with a dose-dependent effect. With respect to CCR5, a concentration of 500 ng/ml gave the highest inhibition of wild-type RANTES activity, while with respect to CCR3, the receptor desensitisation was incomplete (see FIGS. 5 and 6).

The fluorescence signal, induced by changes in intracellular $Ca^{++}$, was monitored with a fluorometer.

What is claimed is:

1. An isolated human RANTES mutant capable of inhibiting macrophage tropic HIV (M-tropic HIV) infection containing a single mutation only, wherein the single mutation is selected from the group consisting of
   a) Arg 44 with Glu;
   b). Lys 45 with Glu;
   c). Tyr 3 with Ala;
   d). Ser 1 with Cys;
   e). Asp 6 with Arg;
   f). Tyr 14 with Phe; and
   g). Mg 17 with Ala.

2. An isolated nucleic acid molecule encoding the isolated human RANTES mutant of claim 1.

3. A vector for eukaryotic or prokaryotic expression comprising the nucleic acid molecule of claim 2.

4. A pharmaceutical composition comprising the isolated human RANTES mutant of claim 1 as the active ingredient.

5. A process for preparing the isolated human RANTES mutant of claim 1, comprising:
   culturing eukaryotic cells transfected with a vector containing a DNA sequence encoding said RANTES mutant to produce said RANTES mutant.

6. A process according to claim 5, wherein said vector is a baculovirus expression vector.

7. A process according to claim 5, wherein said vector is an *Escherichia coli* expression vector.

* * * * *

SEQUENCE LISTING

```
<160> NUMBER OF SEQ ID NOS: 18

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 1
acgaattcac aggtaccatg aaggtctccg cg                               32

<210> SEQ ID NO 2
<211> LENGTH: 34
<212> TYPE: DNA
```

```
<213> ORGANISM: Artificial Sequence
<220> FEATURE:
<223> OTHER INFORMATION: Description of Artificial Sequence:
      oligonucleotide

<400> SEQUENCE: 2
gtggatcctt tttgtaactg ctgctcgtcg tggt                              34

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
caatatgttg ccggcatagt acgcagc                                     27

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
ggatcagatt tgcagcggcc g                                           21

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
gtggatcctt tttgtaactg ctgctcgtcg tggt                              34

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
gggtgtggtg tccgaggaat atgggcaggc ag                               32

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
gtccgaggaa gctggggagg cagatg                                      26

<210> SEQ ID NO 8
<211> LENGTH: 32
<212> TYPE: DNA
<213> ORGANISM: Artificial Sequence
```

```
<220> FEATURE:
<223> OTHER INFORMATION: Description of Artificial Sequence:
      oligonucleotide

<400> SEQUENCE: 8
gggtgtggtg tcgcaggaat atgggcaggc ag                                      32

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
cacggggcag tggggcggca atgtaggcaa agc                                     33

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
cagggtgtgt ggtgcgcgag gaatatgggg a                                       31

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
ggcggttctt ttcggtgaca aagacgac                                           28

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
cttggcggtt ctctcgggtg acaaagacg                                          29

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 13
atatggggat aaggcagatg caggagcgca                                         30

<210> SEQ ID NO 14
<211> LENGTH: 27
<212> TYPE: DNA
<213> ORGANISM: Artificial Sequence
<220> FEATURE:
```

```
-continued

<223> OTHER INFORMATION: Description of Artificial Sequence:
      oligonucleotide

<400> SEQUENCE: 14
tgggcgggca atggcggcaa agcaggg                                              27

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 15
gggtgtggtg tccgagcaat atgggcaggc ag                                        32

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
ccgagcaata tggggagcag gcagatgcag gag                                       33

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17
atatggggag gctaaggcag atgcagga                                             28

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
tgggcgggca atgtaggcaa agcagcaggg                                           30
```